(12) United States Patent
Yaku

(10) Patent No.: US 10,144,973 B2
(45) Date of Patent: Dec. 4, 2018

(54) METHOD FOR DETERMINING WHETHER OR NOT AQUEOUS SOLUTION CONTAINS CANCER CELLS BY USING IMPROVED TELOMERASE ASSAY

(71) Applicant: Panasonic Intellectual Property Management Co., Ltd., Osaka (JP)

(72) Inventor: Hidenobu Yaku, Hyogo (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 214 days.

(21) Appl. No.: 15/257,782

(22) Filed: Sep. 6, 2016

(65) Prior Publication Data

US 2017/0275698 A1 Sep. 28, 2017

(30) Foreign Application Priority Data

Mar. 28, 2016 (JP) .................................. 2016-063007

(51) Int. Cl.
*C12P 19/34* (2006.01)
*C12Q 1/6886* (2018.01)
*C12Q 1/686* (2018.01)

(52) U.S. Cl.
CPC ........... *C12Q 1/6886* (2013.01); *C12Q 1/686* (2013.01)

(58) Field of Classification Search
None
See application file for complete search history.

(56) References Cited

U.S. PATENT DOCUMENTS 5,804,380 A * 9/1998 Harley .................. A61K 31/70
435/183
8,101,357 B2 * 1/2012 Yaku ........................ C12N 9/99
435/6.1

FOREIGN PATENT DOCUMENTS

WO 2004/044246 5/2004

OTHER PUBLICATIONS

Hidenobu Yaku et al., "A Highly Sensitive Telomerase Activity Assay that Eliminates False-Negative Results Caused by PCR Inhibitors" Molecules 2013, vol. 18, pp. 11751-11767.

* cited by examiner

*Primary Examiner* — Kenneth R Horlick
(74) *Attorney, Agent, or Firm* — McDermott Will & Emery LLP

(57) ABSTRACT

The present invention provides a method for determining whether or not an aqueous solution contains two or more cancer cells. The present method is characterized by the following three matters. First, the PCR solution contains the TS primer at a concentration of not less than 0.1 μM and not more than 1 μM in the present invention. Second, the PCR solution contains an ACX reverse primer. Third, the PCR solution contains the ACX reverse primer at a concentration of not less than 0.02 μM and not more than 0.06 μM in the present invention. In the present method, it is determined that an aqueous solution contains cancer cells even if the aqueous solution contains only two cancer cells.

5 Claims, No Drawings

Specification includes a Sequence Listing.

METHOD FOR DETERMINING WHETHER OR NOT AQUEOUS SOLUTION CONTAINS CANCER CELLS BY USING IMPROVED TELOMERASE ASSAY

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

The material contained in the ASCII text filed named "P0466341US01_ST25" created on Jul. 5, 2016 and having a file size of 1096 bytes is incorporated herein by reference.

BACKGROUND

1. Technical Field

The present invention relates to a method for determining whether or not an aqueous solution contains two or more cancer cells.

2. Description of the Related Art

Yaku H. et. al., "A Highly Sensitive Telomerase Activity Assay that Eliminates False-Negative Results Caused by PCR Inhibitors", Molecules, 2013, Vol. 18, pp. 11751-11767 (hereinafter, referred to as "Yaku") discloses a telomerase activity measurement method. In this method, activity of telomerase contained in a biological sample is measured in accordance with the following procedures (I)-(IV).

(I) A telomerase reaction solution containing a biological sample is prepared, and a telomerase reaction is conducted in the telomerase reaction solution. In this way, telomerase reaction products are obtained.

(II) The telomerase reaction products are immobilized on magnetic beads. Then, the magnetic beads are washed.

(III) A DNA sequence contained in the telomerase reaction products is amplified by a PCR method using the thus-bound telomerase reaction products as a template. In this way, PCR products are obtained.

(IV) The PCR products are detected by a cycling probe technology method.

WO 2004/044246 discloses a method and a composition for detecting telomerase activity.

SUMMARY

The present invention provides a method for determining whether or not an aqueous solution contains two or more cancer cells, the method comprising:

(a) adding a TS primer, dTTP, dATP, and dGTP to the aqueous solution to prepare a telomerase reaction solution, wherein the TS primer is a primer represented by the DNA sequence (SEQ ID NO: 01)
5'-AATCCGTCGAGCAGAGTT-3';

(b) leaving the telomerase reaction solution prepared in the step (a) in a condition where a telomerase reaction occurs to obtain telomerase reaction products;

(c) binding the telomerase reaction products obtained in the step (b) to a solid phase;

(d) mixing a DNA polymerase, dTTP, dATP, dGTP, dCTP, the TS primer, and a reverse primer with the telomerase reaction products bound to the solid phase in the step (c) to prepare a PCR solution, wherein the reverse primer is a primer represented by the DNA sequence (SEQ ID NO: 02)
5'-GCGCGGCTTACCCTTACCCTTACCCTAACC-3';

the TS primer contained in the PCR solution has a concentration of not less than 0.1 µM and not more than 1 µM; and the reverse primer contained in the PCR solution has a concentration of not less than 0.02 µM and not more than 0.06 µM;

(e) leaving the PCR solution prepared in the step (d) in a condition where a PCR occurs to obtain PCR products, wherein the TS primer serves as a forward primer in the PCR;

(f) mixing a probe RNA and an RNaseH enzyme with the PCR products obtained in the step (d) to prepare an RNaseH reaction solution, wherein the probe RNA consists of an RNA sequence of 5'-CCCUAACCC-3' (SEQ ID NO: 03), a fluorescent group, and a quenching group;

one end and the other end of the probe RNA are modified with the fluorescent group and the quenching group, respectively; and the quenching group is capable of absorbing fluorescence from the fluorescent group;

(g) leaving the RNaseH reaction solution prepared in the step (f) in a condition where an RNaseH reaction occurs; and (h) observing presence or absence of the fluorescence from the RNaseH reaction solution after the step (g) to determine that the aqueous solution contains two or more cancer cells in a case where the fluorescence is present.

The present invention provides a method for determining that an aqueous solution contains cancer cells even if the aqueous solution contains only two cancer cells.

DETAIL DESCRIPTION OF THE EMBODIMENT

Hereinafter, the present invention will be described in more detail.

The present invention was achieved by improving the telomerase activity measurement method disclosed in Yaku. Three differences between the present invention and Yaku will be listed below as items (I)-(III).

(I) The PCR solution prepared in the step (d) contains the TS primer at a concentration of not less than 0.1 µM and not more than 1 µM in the present invention; whereas the PCR solution contains the TS primer at a concentration of 10 µM in Yaku.

(II) The PCR solution prepared in the step (d) contains a reverse primer represented by the DNA sequence 5'-GCGCGGCTTACCCTTACCCTTACCCTAACC-3' (SEQ ID NO: 02, hereinafter, the reverse primer is referred to as "ACX primer") in the present invention; whereas the PCR solution contains a reverse primer represented by the DNA sequence 5'-GTGCCCTTACCCTTACCCTTAC-CCTAA-3' (SEQ ID NO: 04, hereinafter, the reverse primer is referred to as "CX-ext primer" in Yaku.

(III) The PCR solution prepared in the step (d) contains the reverse primer (i.e., ACX primer) at a concentration of not less than 0.02 µM and not more than 0.06 µM in the present invention; whereas the PCR solution contains the reverse primer (i.e., CX-ext primer") at a concentration of 1 µM in Yaku.

As demonstrated in the inventive examples which will be described later, in the present invention, even if an aqueous solution contains only two cancer cells, it is determined accurately that the aqueous solution contains cancer cells. On the other hand, as demonstrated in the comparative example 6 which will be described later, according to the method disclosed in Yaku, if an aqueous solution contains only two cancer cells, it is impossible to determine that the aqueous solution contains cancer cells.

An example of the cancer cell is a HeLa cell. Hereinafter, the step (a)—the step (h) will be described.

(Step (a))

In the step (a), a TS primer, dTTP, dATP, and dGTP are added to an aqueous solution. In this way, a telomerase reaction solution is prepared.

An example of the aqueous solution is a cell lysate or a tissue lysate obtained by lysing a cell or a biological tissue using a solution containing a surfactant.

The TS primer is a DNA which is a substrate of the telomerase. The TS primer is a primer represented by the DNA sequence 5'-AATCCGTCGAGCAGAGTT-3' (SEQ ID NO: 01).

The terms "dTTP", "dATP", and "dGTP" mean deoxythymidine triphosphate, deoxyadenosine triphosphate, and deoxyguanosine triphosphate, respectively.

In order to prevent the telomerase reaction from being inhibited by a DNase which may be contained in the aqueous solution, it is desirable that a DNA which is not a substrate of telomerase is added to the aqueous solution. An example of the DNA which is not a substrate of telomerase is a λDNA, a plasmid DNA, or a M13 bacteriophage vector. See U.S. patent application Ser. No. 14/743,901, the whole contents of which are incorporated herein by reference. U.S. patent application Ser. No. 14/743,901 was published as WO2015/029340.

(Step (b))

The step (b) is preformed after the step (a). In the step (b), the telomerase reaction solution prepared in the step (a) is left in a condition where a telomerase reaction occurs. In this way, telomerase reaction products are obtained. Specifically, the telomerase reaction solution is left at rest at a temperature of not less than 20 degrees Celsius and not more than 40 degrees Celsius for not less than 30 minutes and not more than 180 minutes.

(Step (c))

The step (c) is preformed after the step (b). The telomerase reaction products obtained in the step (b) are bound to a solid phase. It is desirable that the solid phase is washed after the binding.

An example of the solid phase is a substrate or a particle. The particle may be a magnetic particle.

A method for binding the telomerase reaction products to the solid phase will be briefly described. For more detail, see Yaku.

In a case where a surface of the solid phase is formed of gold, the TS primer used in the step (a) has a thiol group at the 5'-terminus thereof. The telomerase reaction products are bound to gold through a sulfur atom included in the thiol group.

In a case where a surface of the solid phase is formed of avidin (including streptavidin), the TS primer used in the step (a) has a biotin group at the 5'-terminus thereof. The telomerase reaction products are bound to the solid phase due to the affinity between avidin and biotin.

(Step (d))

The step (d) is preformed after the step (c). The telomerase reaction products bound in the step (c) is mixed with a DNA polymerase, dTTP, dATP, dGTP, dCTP, the TS primer, and a reverse primer to give a PCR solution.

An example of the DNA polymerase is a Taq DNA polymerase, a KOD DNA polymerase, a Pfu DNA polymerase, or a Tth DNA polymerase. The term "dCTP" means deoxycytidine triphosphate.

The reverse primer is the ACX primer represented by the DNA sequence 5'-GCGCGGCTTACCCTTACCCTTAC-CCTAACC-3' (SEQ ID NO: 02). In case where the reverse primer is the CX-ext primer represented by the DNA sequence 5'-GTGCCCTTACCCTTACCCTTACCCTAA-3' (SEQ ID NO: 04) as disclosed in Yaku, it is erroneously determined that the aqueous solution contains no cancer cells in spite of the fact that the aqueous solution actually contains two cells. See the comparative example 6 which will be described later.

The TS primer contained in the PCR solution has a concentration of not less than 0.1 μM and not more than 1 μM. In other words, the PCR solution contains the TS primer at a concentration of not less than 0.1 μM and not more than 1 μM. In case where the concentration of the TS primer is more than 1 μM in the step (d), it is erroneously determined that the aqueous solution contains no cancer cells in spite of the fact that the aqueous solution actually contains two cells. See the comparative examples 5-6 which will be described later. In the step (d) of the comparative examples 5-6, the concentration of the TS primer is 2 μM and 10 μM, respectively.

The reverse primer contained in the PCR solution has a concentration of not less than 0.02 μM and not more than 0.06 μM. In other words, the PCR solution contains the reverse primer at a concentration of not less than 0.02 μM and not more than 0.06 μM. In case where the concentration of the reverse primer is more than 0.06 μM in the step (d), it is erroneously determined that the aqueous solution contains no cancer cells in spite of the fact that the aqueous solution actually contains two cells. See the comparative examples 1-3 which will be described later. In the step (d) of the comparative examples 1-3, the concentration of the reverse primer is 0.08 μM, 0.1 μM, and 0.5 μM, respectively. Similarly, in case where the concentration of the reverse primer is less than 0.02 μM in the step (d), it is erroneously determined that the aqueous solution contains no cancer cells in spite of the fact that the aqueous solution actually contains two cells. See the comparative example 4 which will be described later. In the step (d) of the comparative example 4, the concentration of the reverse primer is 0.01 μM.

(Step (e))

The step (e) is preformed after the step (d). The PCR solution prepared in the step (d) is left in a condition where a PCR occurs. In this way, PCR products are obtained. The TS primer mixed in the step (d) serves as a forward primer.

Specifically, in the PCR preformed in the step (e), a PCR cycle is repeated thirty-forty times. One PCR cycle includes a deforming step for deforming a double-stranded DNA to give a single-stranded DNA, an annealing step for binding a primer to a template DNA (i.e., the obtained single-stranded DNA), and a DNA extension reaction step for causing a DNA extension reaction to occur using a DNA polymerase.

The PCR products obtained in the step (e) are roughly divided into a DNA extended from the TS primer (hereinafter, this DNA is referred to as "first DNA") and a DNA extended from the reverse primer (hereinafter, this DNA is referred to as "second DNA"). As mentioned above, the concentration of the TS primer contained in the PCR solution is higher than the concentration of the reverse primer contained in the PCR solution. Therefore, the number of the first DNAs is larger than the number of the second DNAs.

(Step (f))

The step (f) is preformed after the step (e). The PCR products obtained in the step (e) is mixed with a probe RNA and an RNaseH enzyme to give an RNaseH reaction solution.

The probe RNA consists of an RNA sequence of 5'-CCCUAACCC-3' (SEQ ID NO: 03), a fluorescent group, and a quenching group. The probe RNA is capable of being hybridized to the first DNA. The one end and the other end of the probe RNA are modified with the fluorescent group and the quenching group, respectively. In a case where the 5'-terminus of the probe RNA is modified with the fluorescent group, the 3'-terminus of the probe RNA is modified with the quenching group. In a case where the 5'-terminus of the probe RNA is modified with the quenching group, the 3'-terminus of the probe RNA is modified with the fluorescent group.

An example of the fluorescent group is fluorescein isothiocyanate (hereinafter, referred to as "FITC"). An example of the quenching group is 4-[4-(dimethylamino)phenylazo] benzoic acid (hereinafter, referred to as "Dabcyl").

The RNaseH enzyme is a ribonuclease capable of cutting an RNA which has been hybridized to a DNA.

(Step (g))

The step (g) is preformed after the step (f). The RNaseH reaction solution prepared in the step (f) is left in a condition where an RNaseH reaction occurs. Specifically, the RNaseH reaction solution is left at rest at a temperature of 20 degrees Celsius-40 degrees Celsius for 10-60 minutes.

(Step (h))

The step (h) is preformed after the step (g). In the step (h), presence or absence of fluorescence from the RNaseH reaction solution is observed.

If the aqueous solution in the step (a) contains cancer cells such as HeLa cells, a lot of the telomerase reaction products are obtained in the step (b). For this reason, in the step (f), a lot of the first DNAs (i.e., DNAs extended from the TS primer) are obtained. In the step (g), the probe RNA is hybridized to the first DNA obtained in the step (f), and the hybridized probe RNA is cut by the RNaseH enzyme. The cutting of the probe RNA increases the fluorescence intensity from the fluorescent group, since the cutting of the probe RNA increases the distance between the fluorescent group and the quenching group with which the one end and the other end of the probe RNA are modified.

On the other hand, if the aqueous solution in the step (a) contains no cancer cell, no telomerase reaction products are obtained in the step (b). For this reason, in the step (f), no first DNAs are obtained. In the step (g), the probe RNA is not cut by the RNaseH enzyme, since the RNaseH reaction solution contains no first DNA. For this reason, the fluorescence intensity from the fluorescent group is not changed, since the distance between the fluorescent group and the quenching group remains unchanged.

Therefore, in a case where fluorescence from the RNaseH reaction solution is present, it is determined that the aqueous solution contains cancer cells. On the other hand, in a case where fluorescence from the RNaseH reaction solution is absent (or significantly weak), it is determined that the aqueous solution contains no cancer cell. As demonstrated in the inventive examples 1-7 which will be described later, in the present invention, it is determined accurately that the aqueous solution contains cancer cells even if the aqueous solution contains only two cancer cells.

EXAMPLES

Hereinafter, the present invention will be described in more detail with reference to the following examples.

Inventive Example 1

First, telomerase reaction solutions A-D were prepared. Table 1 shows the details of the compositions of telomerase reaction solutions A-D.

TABLE 1

Details of Compositions of Telomerase reaction solutions A-D

|  | Solution A | Solution B | Solution C | Solution D |
|---|---|---|---|---|
| 10x Buffer | 1 µL | 1 µL | 1 µL | 1 µL |
| 50x dNTP mix | 0.2 µL | 0.2 µL | 0.2 µL | 0.2 µL |
| 10 µM B-TS primer | 1 µL | 1 µL | 1 µL | 1 µL |
| 32 µg/mL λDNA | 2.6 µL | 2.6 µL | 2.6 µL | 2.6 µL |
| HeLa cell lysate | 2 µL | 2 µL | 2 µL | 2 µL |
| Number of HeLa cells | 0 | 2 | 20 | 2,000 |
| Pure water | 3.2 µL | 3.2 µL | 3.2 µL | 3.2 µL |
| Total volume | 10 µL | 10 µL | 10 µL | 10 µL |

10× Buffer contained 200 mM of Tris-HCl (pH 8.3), 15 mM of $MgCl_2$, 630 mM of KCl, 0.5% Tween 20, and 10 mM EDTA. These reagents contained in the 10× Buffer were available from Wako Pure Chemical Industries Co., Ltd.

50× dNTP mix contained 2.5 mM dATP, 2.5 mM dTTP, 2.5 mM dCTP, and 2.5 mM dGTP. 50× dNTP mix was available from Merck Millipore company.

The B-TS primer was a TS primer (SEQ ID NO: 01) having the 5'-terminus modified with biotin. The B-TS primer was available from Tsukuba Oligo service Co., Ltd.

λDNA was available from Takara Bio Inc.

An aqueous solution containing HeLa cells (available from Merck Millipore company, the number of the contained HeLa cells was 100,000) was diluted with a CHAPS lysis buffer (available from Merck Millipore company). In this way, three kinds of HeLa cell lysates for the solutions B, C, and D were obtained.

The telomerase reaction solutions A-D were left at rest at a temperature of 37 degrees Celsius for 30 minutes. Then, the telomerase reaction solutions A-D were heated to a temperature of 95 degrees Celsius for 10 minutes. Finally, the telomerase reaction solutions A-D were cooled to 4 degrees Celsius. In this way, telomerase reaction products were obtained.

Then, each of the telomerase reaction solutions A-D was mixed with a magnetic particle solution containing magnetic particles each coated with streptavidin. The magnetic particle solution was available from ThermoFischer Scientific company, as a trade name: Dynabeads M-280 Streptavidin. The magnetic particle solution had a concentration of 20 mg/mL and a volume of 10 µL. In this way, mixture solutions A-D were prepared. Then, the mixture solutions A-D were shaken at a temperature of 25 degrees Celsius for 30 minutes. In this way, the telomerase reaction products were bound onto surfaces of the magnetic particles.

The mixture solutions A-D were left at rest on a magnet. Then, only supernatants were removed, and precipitates containing the magnetic particles were recovered. The magnetic particles contained in the precipitates were washed with a washing liquid containing Tris-HCl (pH: 7.5, 10 mM) and NaCl (1M). The magnetic particles were further washed with pure water.

Then, a PCR solution shown in Table 2 was prepared. Magnetic particles were added to the PCR solution to give PCR solutions A-D.

TABLE 2

Details of Composition of PCR solution

| 10x LA PCR Buffer II (Mg$^{2+}$ plus)) | 2.2 μL |
|---|---|
| 50x dNTP mix | 0.44 μL |
| 10 μM forward primer | 2.2 μL |
| 0.2 μM reverse primer | 2.2 μL |
| 5 U/μL TaKaRa LA Taq HS | 0.22 μL |
| Pure water | 14.74 μL |
| Total volume | 22 μL |

10× LA PCR Buffer II (Mg$^{2+}$ plus) and 5 U/μL TaKaRa LA Taq HS were available from Takara Bio Inc.

The forward primer was a TS primer (SEQ ID NO: 01) without any modification. The reverse primer was a primer represented by the DNA sequence 5'-GCGCGGCTTAC-CCTTACCCTTACCCTAACC-3' (SEQ ID NO: 02). Both the primers were available from Tsukuba Oligo Service Co., Ltd.

The final concentration of the forward primer and the reverse primer contained in each of the PCR solutions A-D was 1 μM and 0.02 μM, respectively.

The PCR solutions A-D were left in a PCR condition shown in Table 3. In this way, a PCR was conducted using the telomerase reaction products bound to the surfaces of the magnetic particles as a template. Subsequently, the PCR solutions A-D were cooled to 4 degrees Celsius. The PCR solutions A-D were left at rest on a magnet. Then, supernatants A-D were collected from the PCR solutions A-D left at rest on the magnet.

TABLE 3

Details of PCR condition

| Number of the cycles | 40 cycles |
|---|---|
| Process included in one cycle | |
| Deforming step | 95 degrees Celsius and 30 seconds |
| Annealing step | 59 degrees Celsius and 30 seconds |
| DNA extension reaction step | 72 degrees Celsius and 30 seconds |

Then, an RNaseH reaction solution shown in Table 4 was prepared. The RNaseH reaction solution was added to each of the supernatants A-D to give RNaseH reaction solutions A-D.

TABLE 4

Details of Composition of RNaseH reaction solution

| 200 mM Tris-HCl (pH 8) | 10 μL |
|---|---|
| 40 mM MgCl$_2$ | 10 μL |
| 1 μM probe RNA | 10 μL |
| Any one of Supernatants A-D | 10 μL |
| 10 U/μL RNaseH | 1 μL |
| Pure water | 59 μL |
| Total volume | 100 μL |

The probe RNA was a probe represented by the RNA sequence 5'-CCCUAACCC-3' (SEQ ID NO: 03). The 5'-terminus and 3'-terminus of the probe RNA were modified with FITC and Dabcyl which serve as the fluorescent group and the quenching group, respectively. The probe RNA was available from Tsukuba Oligo Service Co., Ltd. 10 U/μL RNaseH was available from Takara Bio Inc.

The RNaseH reaction solutions A-D were left at rest at a temperature of 37 degrees Celsius for 20 minutes. In this way, an RNaseH reaction occurred. Then, an EDTA solution (pH: 8, 500 mM, 10 μL) was added to the RNaseH reaction solutions A-D to stop the RNaseH reaction. In this way, the reaction solutions A-D were obtained.

Finally, the fluorescence intensity of each of the reaction solutions A-D was measured using a fluorescence measurement device (available from Tecan Japan company, trade name: Infinite M1000 pro). The excitation wavelength was 482 nanometers. The fluorescence wavelength was 520 nanometers. The measurement temperature was 25 degrees Celsius. Hereinafter, the term "fluorescence intensity" means the value calculated by subtracting a fluorescence intensity value derived from the reaction solution A from a fluorescence intensity value derived from the reaction solution A, B, C or D. Needless to say, the fluorescence intensity of the reaction solution A is equal to 0. In addition, note that the reaction solution A did not contain a cancer cell such as a HeLa cell at all.

The following Table 5 shows the fluorescence intensity of the reaction solutions A-D in the inventive example 1.

TABLE 5

| | Number of HeLa cells | Fluorescence intensity |
|---|---|---|
| Reaction solution A | 0 | 0 |
| Reaction solution B | 2 | 62 |
| Reaction solution C | 20 | 142 |
| Reaction solution D | 2000 | 1038 |

Final concentration of TS primer (SEQ ID NO: 01) in step (d): 1 μM
Final concentration of reverse primer (SEQ ID NO: 02, namely, ACX primer) in step (d): 0.02 μM As is clear from Table 5, in the inventive example 1, the fluorescence intensity is so high that it is determined that the reaction solution contains HeLa cells even when the reaction solution contains only two HeLa cells.

Inventive Example 2

In the inventive example 2, an experiment similar to the inventive example 1 was conducted, except that the final concentration of the reverse primer (SEQ ID NO: 02) in the step (d) was 0.04 μM.

The following Table 6 shows the fluorescence intensity of the reaction solutions A-D in the inventive example 2.

TABLE 6

| | Number of HeLa cells | Fluorescence intensity |
|---|---|---|
| Reaction solution A | 0 | 0 |
| Reaction solution B | 2 | 164 |
| Reaction solution C | 20 | 356 |
| Reaction solution D | 2000 | 1174 |

Final concentration of TS primer (SEQ ID NO: 01) in step (d): 1 μM
Final concentration of reverse primer (SEQ ID NO: 02, namely, ACX primer) in step (d): 0.04 μM As is clear from Table 6, also in the inventive example 2, the fluorescence intensity is so high that it is determined that the reaction solution contains HeLa cells even when the reaction solution contains only two HeLa cells.

Inventive Example 3

In the inventive example 3, an experiment similar to the inventive example 1 was conducted, except that the final concentration of the reverse primer (SEQ ID NO: 02) in the step (d) was 0.06 μM.

The following Table 7 shows the fluorescence intensity of the reaction solutions A-D in the inventive example 3.

TABLE 7

| | Number of HeLa cells | Fluorescence intensity |
|---|---|---|
| Reaction solution A | 0 | 0 |
| Reaction solution B | 2 | 142 |
| Reaction solution C | 20 | 261 |
| Reaction solution D | 2000 | 1027 |

Final concentration of TS primer (SEQ ID NO: 01) in step (d): 1 μM
Final concentration of reverse primer (SEQ ID NO: 02, namely, ACX primer) in step (d): 0.06 μM As is clear from Table 7, also in the inventive example 3, the fluorescence intensity is so high that it is determined that the reaction solution contains HeLa cells even when the reaction solution contains only two HeLa cells.

Inventive Example 4

In the inventive example 4, an experiment similar to the inventive example 1 was conducted, except that the final concentrations of the TS primer (SEQ ID NO: 01) and the reverse primer (SEQ ID NO: 02) in the step (d) were 0.5 μM and 0.02 μM, respectively.

The following Table 8 shows the fluorescence intensity of the reaction solutions A-D in the inventive example 4.

TABLE 8

| | Number of HeLa cells | Fluorescence intensity |
|---|---|---|
| Reaction solution A | 0 | 0 |
| Reaction solution B | 2 | 325 |
| Reaction solution C | 20 | 937 |
| Reaction solution D | 2000 | 1119 |

Final concentration of TS primer (SEQ ID NO: 01) in step (d): 0.5 μM
Final concentration of reverse primer (SEQ ID NO: 02, namely, ACX primer) in step (d): 0.02 μM As is clear from Table 8, also in the inventive example 4, the fluorescence intensity is so high that it is determined that the reaction solution contains HeLa cells even when the reaction solution contains only two HeLa cells.

Inventive Example 5

In the inventive example 5, an experiment similar to the inventive example 1 was conducted, except that the final concentrations of the TS primer (SEQ ID NO: 01) and the reverse primer (SEQ ID NO: 02) in the step (d) were 0.5 μM and 0.06 μM, respectively.

The following Table 9 shows the fluorescence intensity of the reaction solutions A-D in the inventive example 5.

TABLE 9

| | Number of HeLa cells | Fluorescence intensity |
|---|---|---|
| Reaction solution A | 0 | 0 |
| Reaction solution B | 2 | 251 |
| Reaction solution C | 20 | 587 |
| Reaction solution D | 2000 | 1148 |

Final concentration of TS primer (SEQ ID NO: 01) in step (d): 0.5 μM
Final concentration of reverse primer (SEQ ID NO: 02, namely, ACX primer) in step (d): 0.06 μM As is clear from Table 9, also in the inventive example 5, the fluorescence intensity is so high that it is determined that the reaction solution contains HeLa cells even when the reaction solution contains only two HeLa cells.

Inventive Example 6

In the inventive example 6, an experiment similar to the inventive example 1 was conducted, except that the final concentrations of the TS primer (SEQ ID NO: 01) and the reverse primer (SEQ ID NO: 02) in the step (d) were 0.1 μM and 0.02 μM, respectively.

The following Table 10 shows the fluorescence intensity of the reaction solutions A-D in the inventive example 6.

TABLE 10

| | Number of HeLa cells | Fluorescence intensity |
|---|---|---|
| Reaction solution A | 0 | 0 |
| Reaction solution B | 2 | 686 |
| Reaction solution C | 20 | 1173 |
| Reaction solution D | 2000 | 1176 |

Final concentration of TS primer (SEQ ID NO: 01) in step (d): 0.1 μM
Final concentration of reverse primer (SEQ ID NO: 02, namely, ACX primer) in step (d): 0.02 μM As is clear from Table 10, also in the inventive example 6, the fluorescence intensity is so high that it is determined that the reaction solution contains HeLa cells even when the reaction solution contains only two HeLa cells.

Inventive Example 7

In the inventive example 7, an experiment similar to the inventive example 1 was conducted, except that the final concentrations of the TS primer (SEQ ID NO: 01) and the reverse primer (SEQ ID NO: 02) in the step (d) were 0.1 μM and 0.06 μM, respectively.

The following Table 11 shows the fluorescence intensity of the reaction solutions A-D in the inventive example 7.

TABLE 11

| | Number of HeLa cells | Fluorescence intensity |
|---|---|---|
| Reaction solution A | 0 | 0 |
| Reaction solution B | 2 | 199 |
| Reaction solution C | 20 | 490 |
| Reaction solution D | 2000 | 949 |

Final concentration of TS primer (SEQ ID NO: 01) in step (d): 0.1 μM
Final concentration of reverse primer (SEQ ID NO: 02, namely, ACX primer) in step (d): 0.06 μM As is clear from Table 11, also in the inventive example 7, the fluorescence intensity is so high that it is determined that the reaction solution contains HeLa cells even when the reaction solution contains only two HeLa cells.

Comparative Example 1

In the comparative example 1, an experiment similar to the inventive example 1 was conducted, except that the final concentration of the reverse primer (SEQ ID NO: 02) in the step (d) was 0.08 μM.

The following Table 12 shows the fluorescence intensity of the reaction solutions A-D in the comparative example 1.

TABLE 12

| | Number of HeLa cells | Fluorescence intensity |
|---|---|---|
| Reaction solution A | 0 | 0 |
| Reaction solution B | 2 | 0 |

TABLE 12-continued

| | Number of HeLa cells | Fluorescence intensity |
|---|---|---|
| Reaction solution C | 20 | 145 |
| Reaction solution D | 2000 | 914 |

Final concentration of TS primer (SEQ ID NO: 01) in step (d): 1 μM
Final concentration of reverse primer (SEQ ID NO: 02, namely, ACX primer) in step (d): 0.08 μM As is clear from Table 12, in the comparative example 1, the fluorescence intensity is so low that it is erroneously determined that the reaction solution (i.e., the reaction solution B) contains no HeLa cells when the reaction solution contains only two HeLa cells.

Comparative Example 2

In the comparative example 2, an experiment similar to the inventive example 1 was conducted, except that the final concentration of the reverse primer (SEQ ID NO: 02) in the step (d) was 0.1 μM.

The following Table 13 shows the fluorescence intensity of the reaction solutions A-D in the comparative example 2.

TABLE 13

| | Number of HeLa cells | Fluorescence intensity |
|---|---|---|
| Reaction solution A | 0 | 0 |
| Reaction solution B | 2 | 0 |
| Reaction solution C | 20 | 67 |
| Reaction solution D | 2000 | 601 |

Final concentration of TS primer (SEQ ID NO: 01) in step (d): 1 μM
Final concentration of reverse primer (SEQ ID NO: 02, namely, ACX primer) in step (d): 0.1 μM As is clear from Table 13, also in the comparative example 2, the fluorescence intensity is so low that it is erroneously determined that the reaction solution (i.e., the reaction solution B) contains no HeLa cells when the reaction solution contains only two HeLa cells.

Comparative Example 3

In the comparative example 3, an experiment similar to the inventive example 1 was conducted, except that the final concentration of the reverse primer (SEQ ID NO: 02) in the step (d) was 0.5 μM.

The following Table 14 shows the fluorescence intensity of the reaction solutions A-D in the comparative example 3.

TABLE 14

| | Number of HeLa cells | Fluorescence intensity |
|---|---|---|
| Reaction solution A | 0 | 0 |
| Reaction solution B | 2 | 14 |
| Reaction solution C | 20 | 77 |
| Reaction solution D | 2000 | 181 |

Final concentration of TS primer (SEQ ID NO: 01) in step (d): 1 μM
Final concentration of reverse primer (SEQ ID NO: 02, namely, ACX primer) in step (d): 0.5 μM As is clear from Table 14, also in the comparative example 3, the fluorescence intensity is so low that it is erroneously determined that the reaction solution (i.e., the reaction solution B) contains no HeLa cells when the reaction solution contains only two HeLa cells.

Comparative Example 4

In the comparative example 4, an experiment similar to the inventive example 1 was conducted, except that the final concentration of the reverse primer (SEQ ID NO: 02) in the step (d) was 0.01 μM.

The following Table 15 shows the fluorescence intensity of the reaction solutions A-D in the comparative example 4.

TABLE 15

| | Number of HeLa cells | Fluorescence intensity |
|---|---|---|
| Reaction solution A | 0 | 0 |
| Reaction solution B | 2 | 10 |
| Reaction solution C | 20 | 10 |
| Reaction solution D | 2000 | 1085 |

Final concentration of TS primer (SEQ ID NO: 01) in step (d): 1 μM
Final concentration of reverse primer (SEQ ID NO: 02, namely, ACX primer) in step (d): 0.1 μM As is clear from Table 15, also in the comparative example 4, the fluorescence intensity is so low that it is erroneously determined that the reaction solution (i.e., the reaction solutions B and C) contains no HeLa cells when the number of the HeLa cells contained in the reaction solution is not more than 20.

Comparative Example 5

In the comparative example 5, an experiment similar to the inventive example 1 was conducted, except that the final concentrations of the TS primer (SEQ ID NO: 01) and the reverse primer (SEQ ID NO: 02) in the step (d) were 2 μM and 0.02 μM, respectively.

The following Table 16 shows the fluorescence intensity of the reaction solutions A-D in the comparative example 5.

TABLE 16

| | Number of HeLa cells | Fluorescence intensity |
|---|---|---|
| Reaction solution A | 0 | 0 |
| Reaction solution B | 2 | 0 |
| Reaction solution C | 20 | 712 |
| Reaction solution D | 2000 | 797 |

Final concentration of TS primer (SEQ ID NO: 01) in step (d): 2 μM
Final concentration of reverse primer (SEQ ID NO: 02, namely, ACX primer) in step (d): 0.02 μM As is clear from Table 16, also in the comparative example 5, the fluorescence intensity is so low that it is erroneously determined that the reaction solution (i.e., the reaction solution B) contains no HeLa cells, when the reaction solution contains only two HeLa cells.

Comparative Example 6

In the comparative example 6, an experiment similar to the inventive example 1 was conducted, except for the following three matters (I)-(III).

(I) The final concentration of the TS primer in the step (d) was 10 μM.

(II) The reverse primer in the step (d) was a CX-ext primer (SEQ ID NO: 04).

(III) The final concentration of the reverse primer (i.e., CX-ext primer) was 1 μM.

The following Table 17 shows the fluorescence intensity of the reaction solutions A-D in the comparative example 6.

TABLE 17

| | Number of HeLa cells | Fluorescence intensity |
|---|---|---|
| Reaction solution A | 0 | 0 |
| Reaction solution B | 2 | 0 |

TABLE 17-continued

| | Number of HeLa cells | Fluorescence intensity |
|---|---|---|
| Reaction solution C | 20 | 0 |
| Reaction solution D | 2000 | 256 |

Final concentration of TS primer (SEQ ID NO: 01) in step (d): 10 μM
Final concentration of reverse primer (SEQ ID NO: 04, namely, CX-ext primer) in step (d): 1 μM As is clear from Table 17, in the comparative example 6, the fluorescence intensity is so low that it is erroneously determined that the reaction solutions (i.e., the reaction solutions B and C) contain no HeLa cells, when the number of the HeLa cells contained in the reaction solution is not more than 20.

Comparative Example 7

In the comparative example 7, an experiment similar to the inventive example 1 was conducted, except that the final concentrations of the TS primer (SEQ ID NO: 01) and the reverse primer (SEQ ID NO: 02) in the step (d) were 10 μM and 1 μM, respectively.

The following Table 18 shows the fluorescence intensity of the reaction solutions A-D in the comparative example 7.

TABLE 18

| | Number of HeLa cells | Fluorescence intensity |
|---|---|---|
| Reaction solution A | 0 | 0 |
| Reaction solution B | 2 | 21 |
| Reaction solution C | 20 | 11 |
| Reaction solution D | 2000 | 125 |

Final concentration of TS primer (SEQ ID NO: 01) in step (d): 10 μM
Final concentration of reverse primer (SEQ ID NO: 02, namely, ACX primer) in step (d): 1 μM As is clear from Table 18, also in the comparative example 7, the fluorescence intensity is so low that it is erroneously determined that the reaction solutions (i.e., the reaction solutions B and C) contain no HeLa cells, when the number of the HeLa cells contained in the reaction solution is not more than 20.

INDUSTRIAL APPLICABILITY

The present invention can be used to determine whether or not a patient suffers from cancer.

```
                    SEQUENCE LISTING

<110> Panasonic Intellectual Property Management
Co., Ltd.

<120> METHOD FOR DETERMINING WHETHER OR NOT
AQUEOUS SOLUTION CONTAINS TWO OR MORE CANCER
CELLS

<130> P0466341US01

<150> JP2016-063007
<151> 2016-03-28

<160> 4

<170> PatentIn version 3.5

<210> 1
<211> 18
<212> DNA
<213> Artificial Sequence

<220>
<223> Synthesized Primer

<400> 1
aatccgtcga gcagagtt                                           18

<210> 2
<211> 30
<212> DNA
<213> Artificial Sequence

<220>
<223> Synthsized Primer

<400> 2
gcgcggctta cccttaccct taccctaacc                              30

<210> 3
<211> 9
<212> RNA
<213> Artificial Sequence

<220>
<223> Part of Synthesized probe RNA

<400> 3
cccuaaccc                                                      9

<210> 4
<211> 27
<212> DNA
<213> Artificial Sequence

<220>
<223> Synthesized Primer

<400> 4
gtgcccttac ccttaccctt accctaa                                 27
```

```
                    SEQUENCE LISTING

<160> NUMBER OF SEQ ID NOS: 4

<210> SEQ ID NO 1
<211> LENGTH: 18
<212> TYPE: DNA
<213> ORGANISM: Artificial Sequence
<220> FEATURE:
<223> OTHER INFORMATION: Synthesized Primer

<400> SEQUENCE: 1
```

```
aatccgtcga gcagagtt                                                  18

<210> SEQ ID NO 2
<211> LENGTH: 30
<212> TYPE: DNA
<213> ORGANISM: Artificial Sequence
<220> FEATURE:
<223> OTHER INFORMATION: Synthsized Primer

<400> SEQUENCE: 2
gcgcggctta cccttaccct taccctaacc                                     30

<210> SEQ ID NO 3
<211> LENGTH: 9
<212> TYPE: RNA
<213> ORGANISM: Artificial Sequence
<220> FEATURE:
<223> OTHER INFORMATION: Part of Synthesized probe RNA

<400> SEQUENCE: 3 cccuaaccc                                                             9

<210> SEQ ID NO 4
<211> LENGTH: 27
<212> TYPE: DNA
<213> ORGANISM: Artificial Sequence
<220> FEATURE:
<223> OTHER INFORMATION: Synthesized Primer

<400> SEQUENCE: 4
gtgcccttac ccttaccctt accctaa                                        27
```

The invention claimed is:

1. A method for determining whether or not an aqueous solution contains cancer cells, the method comprising:
 (a) adding a TS primer, dTTP, dATP, and dGTP to the aqueous solution to prepare a telomerase reaction solution, wherein
 the TS primer is SEQ ID NO: 01;
 (b) leaving the telomerase reaction solution prepared in the step (a) in a condition where a telomerase reaction occurs to obtain telomerase reaction products;
 (c) binding the telomerase reaction products obtained in the step (b) to a solid phase;
 (d) mixing a DNA polymerase, dTTP, dATP, dGTP, dCTP, the TS primer, and a reverse primer with the telomerase reaction products bound to the solid phase in the step (c) to prepare a PCR solution, wherein
 the reverse primer is SEQ ID NO: 02;
 the TS primer contained in the PCR solution has a concentration of not less than 0.1 µM and not more than 1 µM; and
 the reverse primer contained in the PCR solution has a concentration of not less than 0.02 µM and not more than 0.06 µM;
 (e) leaving the PCR solution prepared in the step (d) in a condition where a PCR occurs to obtain PCR products, wherein
 the TS primer serves as a forward primer in the PCR;
 (f) mixing a probe RNA and an RNaseH enzyme with the PCR products obtained in the step (d) to prepare an RNaseH reaction solution, wherein
 the probe RNA consists of an RNA sequence of 5'-CCCUAACCC-3' (SEQ ID NO: 03), a fluorescent group, and a quenching group;
 one end and the other end of the probe RNA are modified with the fluorescent group and the quenching group, respectively; and
 the quenching group is capable of absorbing fluorescence from the fluorescent group;
 (g) leaving the RNaseH reaction solution prepared in the step (f) in a condition where an RNaseH reaction occurs; and
 (h) observing presence or absence of the fluorescence from the RNaseH reaction solution after the step (g) to determine that the aqueous solution contains cancer cells in a case where the fluorescence is present.

2. The method according to claim 1, wherein
the aqueous solution contains at least one selected from the group consisting of a cell lysate and a tissue lysate.

3. The method according to claim 1, wherein
at least one selected from the group consisting of a λ DNA, a plasmid DNA, and a M13 bacteriophage vector is further added to the aqueous solution in the step (a).

4. The method according to claim 1, wherein
the 5'-terminus of the TS primer added in the step (a) is modified with biotin; and
the solid phase is formed of a magnetic particle coated with streptavidin.

5. The method according to claim 1, wherein
the fluorescent group is formed of fluorescein isothiocyanate; and
the quenching group is formed of 4-[4-(dimethylamino) phenylazo]benzoic acid.

* * * * *